(12) United States Patent
Shalaby

(10) Patent No.: US 6,462,169 B1
(45) Date of Patent: Oct. 8, 2002

(54) AMORPHOUS POLYMERIC POLYAXIAL INITIATORS AND COMPLIANT CRYSTALLINE COPOLYMERS THEREFROM

(75) Inventor: Shalaby W. Shalaby, Anderson, SC (US)

(73) Assignee: Poly-Med, Inc., Pendleton, SC (US)

( * ) Notice: Subject to any disclaimer, the term of this patent is extended or adjusted under 35 U.S.C. 154(b) by 44 days.

(21) Appl. No.: 09/698,527

(22) Filed: Oct. 27, 2000

Related U.S. Application Data

(60) Provisional application No. 60/167,998, filed on Nov. 30, 1999.

(51) Int. Cl.$^7$ ................................................. C08G 63/08
(52) U.S. Cl. ...................... 528/354; 528/355; 528/357; 528/359; 525/415; 623/1.15; 606/228
(58) Field of Search ................................. 528/357, 354, 528/355, 359; 525/415; 623/1.15; 606/228

(56) References Cited

U.S. PATENT DOCUMENTS

| | | | |
|---|---|---|---|
| 4,429,080 A | 1/1984 | Casey et al. ................. 525/415 |
| 4,470,416 A | 9/1984 | Kafrawy et al. ......... 128/335.5 |
| 4,532,928 A | 8/1985 | Bezwada et al. ........ 128/335.5 |
| 4,543,952 A | 10/1985 | Shalaby et al. .......... 128/335.5 |
| 5,133,739 A | 7/1992 | Bezwada et al. ............ 606/230 |
| 5,236,444 A | 8/1993 | Muth et al. .................. 606/230 |
| 5,403,347 A | 4/1995 | Roby et al. .................. 606/230 |
| 5,431,679 A | 7/1995 | Bennett et al. .............. 606/230 |
| 5,468,253 A | 11/1995 | Bezwada et al. ............ 606/228 |
| 5,554,170 A | 9/1996 | Roby et al. .................. 606/230 |
| 5,644,002 A | 7/1997 | Cooper et al. ............... 525/411 |
| 5,713,920 A | 2/1998 | Bezwada et al. ............ 606/230 |
| 5,951,997 A * | 9/1999 | Bezwada et al. ............ 528/354 |
| 6,206,908 B1 * | 3/2001 | Roby .......................... 525/415 |

FOREIGN PATENT DOCUMENTS

| | | | |
|---|---|---|---|
| EP | 0 618 250 A1 | 3/1994 | ........... C08G/63/91 |
| EP | 9 697 427 A2 | 7/1995 | ........... C08G/63/08 |
| EP | 0 712 880 A2 | 11/1995 | ........... C08G/81/00 |
| EP | 0 737 703 A2 | 4/1996 | ......... C08G/63/664 |

OTHER PUBLICATIONS

S. W. Shalaby and H. E. Bair, Chapter 4 of *Thermal Characterization of Polymeric Materials* (E.A. Turi, Ed.) Academic Press, NY, 1981, p. 402.
S. W. Shalaby, Chapter 3 of *Thermal Characterization of Polymeric Materials*, Academic Press, NY, 1981, p. 330.
Correa et al., Sixth World Biomaterials Congress, *Trans Soc. Biomat.*, II, 992 (2000).
L. Mandelkern, *Crystallization of Polymers*, McGraw–Hill Book Company, NY, 1964, pp. 105–106.

* cited by examiner

Primary Examiner—P. Hampton Hightower
(74) Attorney, Agent, or Firm—Leigh P. Gregory

(57) ABSTRACT

An absorbable crystalline, monocentric polyaxial copolymer comprising a central carbon or nitrogen atom and at least three axes, each of which includes an amorphous flexible component adjacent and originating from the central atom and a rigid, crystallizable component extending outwardly from the amorphous, flexible component is disclosed along with the use of such copolymer in medical devices which may contain a bioactive agent.

20 Claims, No Drawings

AMORPHOUS POLYMERIC POLYAXIAL INITIATORS AND COMPLIANT CRYSTALLINE COPOLYMERS THEREFROM

This application claims benefit of provisional application 60/167,998 filed Nov. 30, 1999.

BACKGROUND OF THE INVENTION

Since the successful development of crystalline thermoplastic polyglycolide as an absorbable fiber-forming material, there has been a great deal of effort directed to the development of new linear fiber-forming polyesters with modulated mechanical properties and absorption profiles. Such modulation was made possible through the application of the concept of chain segmentation or block formation, where linear macromolecular chains comprise different chemical entities with a wide range of physicochemical properties, among which is the ability to crystallize or impart internal plasticization. Typical examples illustrating the use of this strategy are found in U.S. Pat. Nos. 5,554,170, 5,431,679, 5,403,347, 5,236,444, and 5,133,739, where difunctional initiators were used to produce linear crystallizable copolymeric chains having different microstructures.

On the other hand, controlled branching in crystalline, homochain polymers, such as polyethylene, has been used as a strategy to broaden the distribution in crystallite size, lower the overall degree in crystallinity and increase compliance (L. Mandelkern, *Crystallization of Polymers*, McGraw-Hill Book Company, NY, 1964, p. 105–106). A similar but more difficult-to-implement approach to achieving such an effect on crystallinity as alluded to above has been used specifically in the production of linear segmented and block heterochain copolymers such as (1) non-absorbable polyether-esters of polybutylene terephthalate and polytetramethylene oxide [see S. W. Shalaby and H. E. Bair, Chapter 4 of *Thermal Characterization of Polymeric Materials* (E. A. Turi, Ed.) Academic Press, NY, 1981, p. 402; S. W. Shalaby et al., U.S. Pat. No. 4,543,952 (1985)]; (2) block/segmented absorbable copolymers of high melting crystallizable polyesters such as polyglycolide with amorphous polyether-ester such as poly-1,5-dioxepane- 2-one (see A. Kafrawy et al., U.S. Pat. No. 4,470,416 (1984)); and (3) block/segmented absorbable copolyesters of crystallizable and non-crystallizable components as cited in U.S. Pat. Nos. 5,554,170, 5,431,679, 5,403,347, 5,236,444, and 5,133,739. However, the use of a combination of controlled branching (polyaxial chain geometry) and chain segmentation or block formation of the individual branches to produce absorbable polymers with tailored properties cannot be found in the prior art. This and recognized needs for absorbable polymers having unique combinations of crystallinity and high compliance that can be melt-processed into high strength fibers and films with relatively brief absorption profiles as compared to their homopolymeric crystalline analogs provided an incentive to explore a novel approach to the design of macromolecular chains to fulfill such needs. Meanwhile, initiation of ring-opening polymerization with organic compounds having three or four functional groups have been used as a means to produce crosslinked elastomeric absorbable systems as in the examples and claims of U.S. Pat. No. 5,644,002. Contrary to this prior art and in concert with the recognized needs for novel crystallizable, melt-processable materials, the present invention deals with the synthesis and use of polyaxial initiators with three or more functional groups to produce crystallizable materials with melting temperatures above 100° C., which can be melt-processed into highly compliant absorbable films and fibers.

SUMMARY OF THE INVENTION

In one aspect the present invention is directed to an absorbable, crystalline, monocentric, polyaxial copolymer which includes a central atom which is carbon or nitrogen and at least three axes originating and extending outwardly from the central atom, with axis including an amorphous, flexible component adjacent to and originating from the central atom, the amorphous component being formed of repeat units derived from at least one cyclic monomer, either a carbonate or a lactone, and a rigid, crystallizable component extending outwardly from the amorphous, flexible component, the crystallizable component being formed of repeat units derived from at least one lactone.

In another aspect the present invention is directed to an absorbable, monocentric, polyaxial copolymer made by a process which includes the steps of:

a) providing a monomeric initiator which is an organic compound selected from the group consisting of tri-functional organic compounds and tetra-functional organic compounds;

b) providing a catalyst based on a multivalent metal;

c) reacting at least one cyclic comonomer selected from the group consisting essentially of carbonates and lactones with the monomeric initiator in the presence of the catalyst such that an amorphous polymeric, polyaxial initiator is formed by ring-opening polymerization of the at least one cyclic comonomer; and d) reacting the amorphous, polymeric polyaxial initiator with at least one lactone comprising a member selected from the group consisting of glycolide, lactide, ρ-dioxanone, and combinations thereof.

DESCRIPTION OF PREFERRED EMBODIMENTS

This invention deals with absorbable, polyaxial, monocentric, crystallizable, polymeric molecules with non-crystallizable, flexible components of the chain at the core and rigid, crystallizable segments at the chain terminals. More specifically, the present invention is directed to the design of amorphous polymeric polyaxial initiators with branches originating from one polyfunctional organic compound so as to extend along more than two coordinates and their copolymerization with cyclic monomers to produce compliant, crystalline film- and fiber-forming absorbable materials. The absorbable copolymeric materials of this invention comprise at least 30 percent, and preferably 65 percent, by weight, of a crystallizable component which is made primarily of glycolide-derived or 1-lactide-derived sequences, and exhibit first and second order transitions below 222° C. and below 42° C., respectively, and undergo complete dissociation into water-soluble by-products in less than 180 days and preferably 120 days when incubated in a phosphate buffer at 37° C. and pH 7.4 or implanted in living tissues.

The amorphous polymeric, polyaxial initiators (PPIs) used in this invention to produce crystalline absorbable copolymeric materials can be made by reacting a cyclic monomer or a mixture of cyclic monomers such as trimethylene carbonate, ε-caprolactone, and 1,5-dioxapane-2-one in the presence of an organometallic catalyst with one or more polyhydroxy, polyamino, or hydroxyamino compound having more than three reactive amines and/or hydroxyl groups. Typical examples of the latter compounds are glycerol, ethane-trimethylol, propane-trimethylol, pentaerythritol, a partially alkylated cyclodextrin, triethanolamine, N-2- aminoethyl-1,3-propanediamine, 3-amino-5-hydroxy pyrazole, and 4-amino-6-ydroxy-2-mercapto-pyrimidine.

The crystalline copolymers of the present invention are so designed to (1) have the PPI devoid of any discernable level of crystallinity; (2) have the PPI component function as a flexible spacer of a terminally placed, rigid, crystallizable component derived primarily from glycolide so as to allow for facile molecular entanglement to create pseudo-crosslinks, which in turn, maximize the interfacing of the amorphous and crystalline fractions of the copolymer leading to high compliance without compromising tensile strength; (3) maximize the incorporation of the hydrolytically labile glycolate linkage in the copolymer without compromising the sought high compliance-this is achieved by directing the polyglycolide segments to grow on multiple active sites of the polymeric initiator and thus limiting the length of the crystallizable chain segments; (4) have a broad crystallization window featuring maximum nucleation sites and slow crystallite growth that in turn assists in securing a highly controlled post-processing and development of mechanical properties—this is achieved by allowing the crystallizable components to entangle effectively with non-crystallizable components leading to high affinity for nucleation, high pre-crystallization viscosity, slow chain motion, and low rate of crystallization; (5) force the polymer to form less perfect crystallites with broad size distribution and lower their melting temperature as compared to their homopolymeric crystalline analogs to aid melt-processing—this is achieved by limiting the length of the crystallizable segments of the copolymeric chain as discussed earlier; (6) allow for incorporating basic moieties in the PPI which can affect autocatalytic hydrolysis of the entire system which in turn accelerates the absorption rate; and (7) allow the polymer chain to associate so as to allow for endothermic thermal events that can be related to tensile toughness similar to that detected in PET relative to the so-called middle endothermic peak (MEP) (S. W. Shalaby, Chapter 3 of *Thermal Characterization of Polymeric Materials*, Academic press, NY, 1981, p. 330).

As an example, the crystalline copolymeric materials of the present invention may be prepared as follows, although as noted above, other monomers are also within the scope of the present invention. The amorphous polymeric polyaxial initiator is formed by a preliminary polymerization of a mixture of $\epsilon$-caprolactone and trimethylene carbonate in the presence of trimethylol-propane and a catalytic amount of stannous octoate, using standard ring-opening polymerization conditions which entail heating the stirred reactants in nitrogen atmosphere at a temperature exceeding 110° C. until substantial or complete conversion of the monomers is realized. This can be followed by adding a predetermined amount of glycolide. Following the dissolution of the glycolide in the reaction mixture, the temperature is raised above 150° C. to allow the glycolide to copolymerize with the polyaxial initiator. When practically all the glycolide is allowed to react, the resulting copolymer is cooled to 25° C. After removing the polymer from the reaction kettle and grinding, trace amounts of unreacted monomer are removed by heating under reduced pressure. The ground polymer can then be extruded and pelletized prior to its conversion to fibers or films by conventional melt-processing methods. At the appropriate stage of polymerization and product purification, traditional analytical methods, such as gel-permeation chromatography (GPC), solution viscosity, differential scanning calorimetry (DSC), nuclear magnetic resonance (NMR), and infrared spectroscopy (IR) are used to monitor or determine (directly or indirectly) the extent of monomer conversion, molecular weight, thermal transitions (melting temperature, Tm, and glass transition temperature, Tg), chain microstructure, and chemical entity, respectively.

Another aspect of this invention deals with end-grafting a PPI with $\epsilon$-caprolactone or 1-lactide, and preferably in the presence of a minor amount of a second monomer, to produce absorbable crystalline polymers for use as bone sealants or barrier membranes, respectively.

Films made by compression molding of the copolymers described in the examples set forth below are evaluated for (1) tensile strength; (2) in vitro breaking strength retention and mass loss during incubation in a phosphate buffer at 37° C. and pH 7.4; (3) in vivo breaking strength retention using a rat model where strips of the films are implanted subcutaneously for 1 to 6 weeks and individual lengths are explanted periodically to determine percent of retained breaking strength; and (4) in vivo absorption (in terms of mass loss) using a rat model where a film strip, inserted in a sealed polyethylene terephthalate (PET) woven bag, is placed in the peritoneum for 6, 8, 10, 12 and 14 weeks. At the end of each period, the PET bag is removed and the residual mass of the strips is removed, rinsed with water, dried, and its weight is determined.

Specifically, an important aspect of this invention is the production of compliant absorbable films with modulated absorption and strength loss profiles to allow their use in a wide range of applications as vascular devices or components therefor; more specifically is the use of these devices in sealing punctured blood vessels.

In another aspect, this invention is directed to the use of the polymers described herein for the production of extruded or molded films for use in barrier systems to prevent post-surgical adhesion or compliant covers, sealants, or barriers for bums and ulcers as well as compromised/damaged tissue. The aforementioned articles may also contain one or more bioactive agent to augment or accelerate their functions. In another aspect, this invention is directed to melt-processed films for use to patch mechanically compromised blood vessels. In another aspect, this invention is directed to the use of the polymer described herein as a coating for intravascular devices such as catheters and stents. In another aspect, this invention is directed to the application of the polymers described herein in the production of extruded catheters for use as transient conduits and microcellular foams with continuous porous structure for use in tissue engineering and guiding the growth of blood vessels and nerve ends. Another aspect of this invention is directed to the use of the polymers described herein to produce injection molded articles for use as barriers, or plugs, to aid the function of certain biomedical devices used in soft and hard tissues and which can be employed in repairing, augmenting, substituting or redirecting/assisting the functions of several types of tissues including bone, cartilage, and lung as well as vascular tissues and components of the gastrointestinal and urinogenital systems. In another aspect, this invention is directed to the use of polymers described herein to produce compliant, melt-blown fabrics and monofilament sutures with modulated absorption and strength retention profiles.

In one aspect of this invention, the subject copolymers are converted to different forms of absorbable stents, such as those used (1) as an intraluminal device for sutureless gastrointestinal sutureless anastomosis; (2) in laparoscopic replacement of urinary tract segments; (3) as an intraluminal device for artery welding; (4) in the treatment of urethral lesions; (5) as a tracheal airway; (6) in the treatment of recurrent urethral strictures; (7) for vasectomy reversal; (8) in the treatment of tracheal stenoses in children; (9) for vasovasostomy; (10) for end-to-end ureterostomy; and (11) as biliary devices.

In another aspect of this invention, the subject copolymers are converted to a highly compliant, expandable tubular mantle, sleeve or cover that is placed tightly outside an expandable metallic or polymeric stent so that under concentric irreversible expansion at the desired site of a treated biological conduit, such as a blood vessel or a urethra, both components will simultaneously expand and the mantle provides a barrier between the inner wall of the conduit and the outer wall of the stent. In another aspect of this invention, the subject copolymers are used as a stretchable matrix of a fiber-reinforced cover, sleeve, or mantle for a stent, wherein the fiber reinforcement is in the form of spirally coiled yarn (with and without crimping) woven, knitted, or braided construct. In another aspect of this invention, the stent mantle, or cover, is designed to serve a controlled release matrix of bioactive agents such as those used (1) for inhibiting neointima formation as exemplified by hirudin and the prostacyclic analogue, iloprost; (2) for inhibiting platelet aggregation and thrombosis; (3) for reducing intraluminal and particular intravascular inflammation as exemplified by dexamethasone and non-steroidal inflammatory drugs, such as naproxen; and (4) for suppressing the restenosis.

One aspect of this invention deals with the conversion of the subject copolymers into molded devices or components of devices used as a hemostatic puncture closure device after coronary angioplasty.

It is further within the scope of this invention to incorporate one or more medico-surgically useful substances into the copolymers and devices subject of this invention. Typical examples of these substances are those capable of (1) minimizing or preventing platelet adhesion to the surface of vascular grafts; (2) rendering anti-inflammatory functions; (3) blocking incidents leading to hyperplasia as in the case of synthetic vascular grafts; (4) aiding endothelialization of synthetic vascular grafts; (5) preventing smooth muscle cell migration to the lumen of synthetic vascular grafts; and (6) accelerating guided tissue ingrowth in fully or partially absorbable scaffolds used in vascular tissue engineering.

In order that those skilled in the art may be better able to practice the present invention, the following illustrations of the preparation of typical crystalline copolymers are provided.

EXAMPLE 1

Synthesis of 20/25 (molar) ε-Caprolactone/ Trimethylene Carbonate Copolymer as a Tri-axial Initiator and Reaction with 55 Relative Molar Parts of Glycolide An initial charge consisted of 142.4 grams (1.249 moles) ε-caprolactone, 159.4 grams (1.563 moles) trimethylene carbonate, 1.666 grams ($1.24 \times 10^{-2}$ moles) trimethylolpropane, and 1.0 ml ($2.03 \times 10^{-4}$ moles) of a 0.203M solution of stannous octoate catalyst in toluene after flame drying the reaction apparatus. The reaction apparatus was a 1 L stainless steel kettle with 3-neck glass lid equipped with an overhead mechanical stirring unit, vacuum adapter, and two 90° connectors for an argon inlet.

The apparatus and its contents were heated to 50° C. under vacuum with a high temperature oil bath. Upon complete melting of the contents after 30 minutes, the system was purged with argon, stirring initiated at 32 rpm, and the temperature set to 150° C. After 4 hours at 150° C., the viscosity of the polyaxial polymeric initiator (PPI) had increased and the temperature of the bath was reduced to 110° C. Upon reaching 110° C., 398.5 grams (3.435 moles) of glycolide were added to the system. When the glycolide had completely melted and mixed into the polyaxial polymeric initiator, the temperature was increased to 180° C. and stirring was stopped. The reaction was allowed to continue for 2 hours before cooling the system to 50° C. and maintaining the heat overnight. The polymer was isolated, ground, dried, extruded and redried as described below in Example 5.

The extrudate was characterized as follows: The inherent viscosity using hexafluoro-isopropyl alcohol (HFIP) as a solvent was 0.97 dL/g. The melting temperature and heat of fusion, as determined by differential scanning calorimetry (using initial heating thermogram), were 215° C. and 40.8 J/g, respectively.

EXAMPLE 2

Synthesis of 25/30 (molar) ε-Caprolactone/ Trimethylene Carbonate Copolymer as a Tri-axial Initiator and Reaction with 45 Relative Molar Parts of Glycolide An initial charge consisted of 122.8 grams (1.077 moles) ε-caprolactone, 131.9 grams (1.292 moles) trimethylene carbonate, 1.928 grams ($1.44 \times 10^{-2}$ moles) trimethylolpropane, and 1.0 ml ($8.62 \times 10^{-5}$ moles) of a 0.086M solution of stannous octoate catalyst in toluene after flame drying the reaction apparatus. The reaction apparatus was a 1 L stainless steel kettle with 3-neck glass lid equipped with an overhead mechanical stirring unit, vacuum adapter, and two 90° connectors for an argon inlet.

The apparatus and its contents were then heated to 65° C. under vacuum with a high temperature oil bath. After 30 minutes, with the contents completely melted, the system was purged with argon, stirring initiated at 34 rpm, and the temperature set to 140° C. After 3 hours at 140° C., the temperature was raised to 150° C. for 1 hour and then reduced back to 140° C. At this point, 225.0 grams (1.940 moles) of glycolide were added to the system while rapidly stirring. When the glycolide had completely melted and mixed into the polyaxial polymeric initiator, the temperature was increased to 180° C. and stirring was stopped. The reaction was allowed to continue for 2 hours before cooling the system to room temperature overnight. The polymer was isolated, ground, dried, extruded, and redried as described in Example 5.

Characterization of the extrudate was conducted as follows: The inherent viscosity using HFIP as a solvent was 0.93 dL/g. The melting temperature and heat of fusion, as measured by differential scanning calorimetry (DSC using initial heating thermogram), were 196° C. and 32.1 J/g, respectively.

EXAMPLE 3

Synthesis of 20/25/3 (molar) ε-Caprolactone/ Trimethylene Carbonate/Glycolide Copolymer as a Tri-axial Initiator and Reaction with 52 Relative Molar Parts of Glycolide An initial charge consisted of 101.6 grams (0.891 moles) ε-caprolactone, 113.5 grams (1.113 moles) trimethylene carbonate, 15.5 grams of glycolide (0.134 moles), 1.996 grams (1.49×10–2 moles) trimethylol-propane, and 1.0 ml (1.28×10$^{-4}$ moles) of a 0.128M solution of stannous octoate catalyst in toluene after flame drying the reaction apparatus. The reaction apparatus was a 1 L stainless steel kettle with 3-neck glass lid equipped, an overhead mechanical stirring unit, vacuum adapter, and two 90° connectors for an argon inlet.

The apparatus and its contents were then heated to 85° C. under vacuum with a high temperature oil bath. After 30 minutes, with the contents completely melted, the system was purged with argon, stirring initiated at 34 rpm, and the temperature set to 140° C. After 4 hours at 140° C., 268.8 grams (2.317 moles) of glycolide were added to the system while rapidly stirring. When the glycolide had completely melted and mixed into the polyaxial polymeric initiator, the temperature was increased to 180° C. and stirring was stopped. The reaction was allowed to continue for 2 hours before cooling the system to room temperature overnight. The polymer was isolated, ground, dried, extruded and redried as in Example 5.

The extrudate was characterized as follows: The inherent viscosity using HFIP as a solvent was 0.89 dL/g. The melting temperature and heat of fusion, as measured by differential scanning calorimetry (DSC using initial heating thermogram), were 212° C. and 34 J/g, respectively.

EXAMPLE 4

Synthesis of 20/25/3 (molar) ε-Caprolactone/ Trimethylene-Carbonate/Glycolide Copolymer as a Tri-axial Initiator and Reaction with 52 Relative Molar Parts of Glycolide Glycolide (18.6 g, 0.1603 mole), TMC (136.7 g, 1.340 mole), ε-caprolactone (122.0 g, 1.070 mole), trimethylol-propane (2.403 g, 0.01791 mole) and stannous octoate catalyst (0.2M in toluene, 764 μL, 0.1528 mmol) were added under dry nitrogen conditions to a 1.0 liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (322.5 g, 2.780 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was isolated, ground, redried, and extruded as described in Example 5. The extrudate was characterized by NMR and IR for identity and DSC (using initial heating thermogram) for thermal transition ($T_m$=208° C., ΔH=28.0 J/g) and solution viscosity in hexafluoroisopropyl alcohol (η=0.92 dL/g).

EXAMPLE 5

Size Reduction and Extrusion of Polymers of Examples 1 through 4

The polymer was quenched with liquid nitrogen and mechanically ground. The ground polymer was dried under vacuum at 25° C. for two hours, at 40° C. for two hours, and at 80° C. for four hours. The polymer was melt extruded at 225° C. to 235° C. using a ½ inch extruder equipped with a 0.094 in die. The resulting filaments were water cooled. The average filament diameter was 2.4 mm. The filament was dried at 40° C. and 80° C. under vacuum for eight and four hours, respectively.

EXAMPLE 6

Compression-molding of Polymers from Examples 3 and 4 to a Sealing Device for a Punctured Blood Vessel and Its Packaging The compression molding process entailed exposing the polymer to an elevated temperature between two mold halves. When temperature of the mold halves exceeded the polymer melting temperature, pressure was applied to the mold and the material was allowed to flow into a predefined cavity of the mold. The mold was then cooled to room temperature before it was opened and the newly shaped polymer was removed.

The full molding cycle can be described as: (1) Drying—typical: temperature 80° C. during 2 hours; (2) Pre-heating, temperature increase—typical: pressure 5,000N, temperature from room temperature up to 200° C.; (3) Forming, constant temperature under high pressure—typical: pressure 50,000N, temperature 200° C.; (4) Cooling, temperature decrease under high pressure—typical: pressure 50,000N, temperature from 200° C. down to 50° C.; (5) Mold opening; (6) Annealing—typical: temperature 80° C. during 2 hours; and (7) Packaging—typically the device was removed from the mold and packaged under vacuum under a protective gas environment.

EXAMPLE 7

Synthesis of 13.3/17.7/2 (molar) Caprolactone/ Trimethylene Carbonate/ Glycolide Copolymer as a Tri-axial Initiator and Reaction with Relative 67 Molar Parts of Glycolide Glycolide (10.4 g, 0.090 mole), TMC (76.5 g, 0.750 mole), ε-caprolactone (68.4 g, 0.600 mole), trimethylolpropane (1.995 g, .01487 mole) and stannous octoate catalyst (0.2M in toluene, 637 μL, 0.1274 mmole) were added under dry nitrogen conditions to a 1.0 liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (344.5 g, 2.970 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was characterized by NMR and IR (for identity), DSC thermal transition ($T_m$=215.7) and solution viscosity in hexafluoroisopropyl alcohol (η–0.95 dL/g).

EXAMPLE 8

Synthesis of 13.6/17.0/2.0 (molar) ε-Caprolactone/ Trimethylene Carbonate/Glycolide Copolymer as a Basic Tri-axial Initiator and Reaction with Relative 67.4 Molar Parts of Glycolide and Trimethylene Carbonate Glycolide (3.1 g, 0.0267 mole), TMC (23.0 g, 0.2255 mole), ε-caprolactone (20.5 g, 0.1798 mole), triethanolamine (0.6775 g, 4.55 mmole) and stannous octoate catalyst (0.2M in toluene, 519 μL, 0.1038 mmole) were added under dry nitrogen conditions to a 0.5 Liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (103.4 g, 0.8914 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was characterized for identity and composition (IR and NMR, respectively) and thermal transition by DSC ($T_m$220° C.) and molecular weight by solution viscometry ($\eta$=0.80 in hexafluoroisopropyl alcohol).

EXAMPLE 9

Synthesis of 13.6/17.0/2.0 (molar) ε-Caprolactone/ Trimethylene Carbonate/Glycolide Copolymer as a Basic Tri-axial Initiator and Reaction with Relative 67.4 Molar Parts of Glycolide The two-step polymerization was conducted as in Example 8 with the exception of using 0.6915 g triethanolamine and 693 μl of stannous octanoate solution. The final polymer was isolated and characterized as in Example 8 and it was shown to have a $T_m$=221° C. and inherent viscosity (in HFIP)=0.82.

EXAMPLE 10

Synthesis of 13.3/17.7/2 (molar) ε-Caprolactone/ Trimethylene Carbonate/Glycolide Copolymer as a Tetra-axial Initiator and Reaction with Relative 67 Molar Parts of Glycolide Glycolide (3.1 g, 0.0267 mole), TMC (23.0 g, 0.2255 mole), ε-caprolactone (20.5 g, 0.1796 mole), pentaerythritol (0.600 g., 0.0044 mole) and stannous octoate catalyst (0.2 M in toluene, 193 μl, 0.0386 mmol) were placed under dry nitrogen conditions to a 0.5 L stainless steel reaction kettle equipped with a glass top and a mechanical stirrer. The polymerization charge was dried at 25° C. and 40° C. under reduced pressure for 60 and 30 minutes, respectively. The reactants were then melted at 85° C. and the system was purged with dry nitrogen. The melt was heated to 160° C. with stirring at 30 rpm. Samples of the prepolymer melt were taken periodically and analyzed for monomer content using GPC (gel permeation chromatography). Once the monomer content of the polymer melt was found to be negligible, glycolide (103.4 g., 0.8914 mole) was added with rapid stirring that is more than 40 rpm. The stirring rate was then lowered to 30 rpm after the contents were well mixed. The reactants were heated to 180° C. Stirring was stopped upon solidification of the polymer. The polymer was heated for 2 hours at 180° C. after solidification. The resulting polymer was cooled to room temperature, quenched in liquid nitrogen, isolated, and dried at 25° C. and then 40° C. under reduced pressure.

The final polymer was isolated and characterized as in Example 8 and it was shown to have a $T_m$=219° C. and inherent viscosity (in HFIP)=0.98.

EXAMPLE 11

Size Reduction and Extrusion of Polymer from Examples 7 through 10

The polymer was quenched with liquid nitrogen and mechanically ground. The ground polymer was dried under vacuum at 25° C. for two hours, at 40° C. for two hours, and at 80° C. for four hours. The polymer was melt extruded at 235° C. to 245° C. using a ½ inch extruder equipped with a 0.094 in die. The resulting monofilament was quenched in an ice-water bath before winding. The monofilament was dried at 40° C. and under vacuum for four hours before orientation.

EXAMPLE 12

Orientation of Melt-spun Monofilaments

Polymers of Examples 7 through 10 that have been extruded as described in Example 11 were oriented by two-stage drawing into monofilament sutures. Prior to drawing Example 7, monofilaments were pre-tensioned and annealed. The drawing was conducted at 90–100° C. in the first stage and 100–130° C. in the second stage. The overall draw ratio varied between 3.73× and 4.6×. A number of monofilaments were relaxed at 70° C. for 15 minutes to reduce their free shrinkage. Properties of the oriented monofilaments are summarized in Table I.

TABLE I

Drawing Conditions and Fiber Properties of Polymers from Examples 7 through 9

| Origin of Extruded Polymer | | Fiber Number | Draw Ratio | Draw Temp. (S1/S2) | Pre-Draw Annealing (min/° C.) | Post-Draw Relaxation (%) | Free Shrinkage (%) | Diameter (mil) | Straight Strength (Kpsi) | Modulus (Kpsi) | Elongation (%) |
|---|---|---|---|---|---|---|---|---|---|---|---|
| Example | 7 | 7F-1 | 3.73X | 95/130 | 35/65 | — | 4.4 | 13.4 | 75 | 444 | 22 |
|  | 7 | 7F-2 | 3.73X | 95/130 | 35/65 | 2.3 | 1.8 | 15.1 | 53 | 182 | 36 |
|  | 7 | 7F-3 | 4.14X | 95/120 | 30/65 | — | 4.2 | 10.2 | 66 | 434 | 19 |
|  | 7 | 7F-4 | 4.14X | 95/120 | 30/65 | 3 | 1.5 | 11.0 | 61 | 257 | 31 |
|  | 8 | 8F-1 | 4.50X | 100/120 | — | — | 3.1 | 10.2 | 71 | 195 | 26 |
|  | 9 | 9F-1 | 4.43X | 100/130 | — | — | 2.1 | 10.6 | 72 | 230 | 27 |
|  | 10 | 10F-1 | 4.60X | 95/120 | — | — | 2.4 | 12.6 | 57 | 158 | 25 |

EXAMPLE 13

Sterilization of Monofilament Sutures and Evaluation of Their In Vitro Breaking Strength Retention Monofilament sutures Numbers 8F-1 and 9F-1 described in Table I were radiochemically sterilized in hermetically sealed foil packages that have been pre-purged with dry nitrogen gas, using 5 and 7.5 KGy of gamma radiation. The radiochemical sterilization process entails the use of 200–400 mg of Delrin (poly-formaldehyde) film as package inserts for the controlled release, radiolytically, of formaldehyde gas as described earlier by Correa et al., [Sixth World Biomaterials Congress, Trans Soc. Biomat., II, 992 (2000)]. The sterile monofilament sutures were incubated in a phosphate buffer at 37° C. and pH 7.4 to determine their breaking strength retention profile as absorbable sutures. Using the breaking strength data of non-sterile sutures (Table I), the breaking strength retention data of sterile sutures were calculated. A summary of these data are given in Table II. These data indicate all sutures retained measurable strength at two weeks in the buffer solution.

TABLE II

Tensile Properties and In Vitro Breaking Strength Retention (BSR) of Radiochemically Sterilized Monofilament Sutures

| Suture Number | 9F-1 | | 8F-1 | |
| --- | --- | --- | --- | --- |
| Sterilization Dose (KGy) | 5 | 7.5 | 5 | 7.5 |
| Post-irradiation Tensile Properties | | | | |
| Tensile Strength (Kpsi) | 66 | 68 | 67 | 65 |
| Modulus (Kpsi) | 266 | 254 | 269 | 263 |
| Elongation (Kpsi) | 30 | 35 | 31 | 30 |
| BSR, % at | | | | |
| Week 1 | 70 | 57 | 82 | 72 |
| Week 2 | 24 | 22 | 18 | 17 |

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:

1. An absorbable, crystalline, monocentric, polyaxial copolymer comprising:
    a central atom selected from the group consisting of carbon and nitrogen; and
    at least three axes originating and extending outwardly from the central atom,
    each axis comprising:
        an amorphous, flexible component adjacent to and originating from the central atom, the amorphous component comprising repeat units derived from at least one cyclic monomer selected from the group consisting essentially of carbonates and lactones; and
        a rigid, crystallizable component extending outwardly from the amorphous, flexible component, the crystallizable component comprising repeat units derived from at least one lactone.

2. The polyaxial copolymer set forth in claim 1 wherein the amorphous component comprises repeat units derived from ε-caprolactone.

3. The polyaxial copolymer set forth in claim 1 wherein the amorphous component comprises repeat units derived from trimethylene carbonate.

4. The polyaxial copolymer set forth in claim 2 wherein the amorphous component further comprises repeat units derived from trimethylene carbonate.

5. The polyaxial copolymer set forth in claim 2 wherein the amorphous component further comprises repeat units derived from glycolide.

6. The polyaxial copolymer set forth in claim 3 wherein the amorphous component further comprises repeat units derived from glycolide.

7. The polyaxial copolymer set forth in claim 4 wherein the amorphous component further comprises repeat units derived from glycolide.

8. The polyaxial copolymer set forth in claim 1 wherein the crystallizable component comprises repeat units derived from glycolide.

9. The polyaxial copolymer set forth in claim 8 wherein the crystallizable component further comprises repeat units derived from a second comonomer selected from the group consisting of trimethylene carbonate, ε-caprolactone, l-lactide, ρ-dioxanone, and 1,5 dioxepane-2-one.

10. The polyaxial copolymer set forth in claim 1 wherein said copolymer comprises a suture.

11. The polyaxial copolymer set forth in claim 1 wherein said copolymer comprises a molded article for sealing punctured blood vessels.

12. The polyaxial copolymer set forth in claim 1 wherein said copolymer comprises a compliant cover for a stent.

13. An absorbable, monocentric, polyaxial copolymer made by the process comprising the steps of:
    e) providing a monomeric initiator comprising an organic compound selected from the group consisting of tri-functional organic compounds and tetra-functional organic compounds;
    f) providing a catalyst comprising a multivalent metal;
    g) reacting at least one cyclic comonomer selected from the group consisting essentially of carbonates and lactones with the monomeric initiator in the presence of the catalyst such that an amorphous polymeric, polyaxial initiator is formed by ring-opening polymerization of the at least one cyclic comonomer; and
    h) reacting the amorphous, polymeric polyaxial initiator with at least one lactone comprising a member selected from the group consisting of glycolide, lactide, ρ-dioxanone, and combinations thereof.

14. The polyaxial copolymer set forth in claim 13 wherein the at least one cyclic comonomer comprises ε-caprolactone.

15. The polyaxial copolymer set forth in claim 13 wherein the at least one cyclic comonomer comprises trimethylene carbonate.

16. The polyaxial copolymer set forth in claim 14 wherein the at least one cyclic comonomer further comprises trimethylene carbonate.

17. The polyaxial copolymer set forth in claim 14 wherein the at least one cyclic comonomer further comprises glycolide.

18. The polyaxial copolymer set forth in claim 15 wherein the at least one cyclic comonomer further comprises glycolide.

19. The polyaxial copolymer set forth in claim 16 wherein the at least one cyclic comonomer further comprises glycolide.

20. The polyaxial copolymer set forth in claim 13 wherein the step of reacting the amorphous, polymeric polyaxial initiator with at least one lactone further comprises reaction with a second comonomer selected from the group consisting of trimethylene carbonate, $\epsilon$-caprolactone, and 1,5 dioxepane-2-one.

* * * * *